000
United States Patent [19]

Brown et al.

[11] 4,431,455
[45] Feb. 14, 1984

[54] WAX DISPERSIONS AND THEIR USE IN THE MANUFACTURE OF SHEETS OR MOULDED BODIES

[75] Inventors: James P. Brown, Manchester; Robert S. Hampson; Frederick T. Kelly, both of Oldham, all of England

[73] Assignee: Imperial Chemical Industries PLC, London, England

[21] Appl. No.: 341,177

[22] Filed: Jan. 20, 1982

[30] Foreign Application Priority Data

Feb. 4, 1981 [GB] United Kingdom ............... 8103439

[51] Int. Cl.$^3$ ............................................. C08L 91/00
[52] U.S. Cl. .................................... 106/245; 106/268; 264/300; 528/74.5
[58] Field of Search ............................ 162/172, 164.6; 106/245, 268, 271; 524/871; 264/300; 156/289, 62.2; 528/73.5

[56] References Cited

U.S. PATENT DOCUMENTS

| 2,844,554 | 7/1958 | Nichols | 524/279 |
|---|---|---|---|
| 3,440,224 | 4/1969 | Impola | 528/48 |
| 3,677,808 | 7/1972 | Sheridan | 106/96 |
| 3,743,617 | 7/1973 | Kest | 524/274 |
| 3,880,975 | 4/1975 | Lundmark | 264/119 |
| 4,033,912 | 7/1977 | Kliemann et al. | 264/300 |
| 4,130,698 | 12/1978 | Sparrow et al. | 264/300 |
| 4,254,228 | 3/1981 | Kliemann et al. | 264/300 |
| 4,257,995 | 3/1981 | McLaughlin et al. | 264/122 |
| 4,257,996 | 3/1981 | Farrissey et al. | 264/122 |

FOREIGN PATENT DOCUMENTS

| 2805951 | 8/1979 | Fed. Rep. of Germany . |
|---|---|---|
| 397834 | 11/1977 | Sweden . |
| 1523601 | 3/1976 | United Kingdom . |

*Primary Examiner*—Theodore Morris
*Attorney, Agent, or Firm*—Cushman, Darby & Cushman

[57] ABSTRACT

An organic polyisocyanate composition contains from 99 to 60 parts by weight of a liquid organic polyisocyanate and from 1 to 40 parts of a 90:10 to 10:90 mixture of a wax and a liquid ester having a molecular weight of at least 250, for example an alkyl ester of an aliphatic carboxylic acid derived from an alkyl alcohol containing from 3 to 30 carbon atoms and a saturated or unsaturated fatty acid containing from 10 to 25 carbon atoms. The composition is useful for the manufacture of sheets or moulded bodies by the hot-pressing of a lignocellulosic material and promotes release of the material from the press. The composition is preferably applied in the form of an aqueous emulsion.

6 Claims, No Drawings

WAX DISPERSIONS AND THEIR USE IN THE MANUFACTURE OF SHEETS OR MOULDED BODIES

This invention relates to wax dispersions and their use in the manufacture of sheets or moulded bodies.

The use of organic polyisocyanates as binders for ligno-cellulosic material in the manufacture of sheets or moulded bodies such as chipboard, fibreboard and plywood is well known.

In a typical process, the organic polyisocyanate, optionally in the form of a solution or an aqueous emulsion, is applied to the ligno-cellulosic material which is then subjected to heat and pressure. The high quality of the resulting articles is due, to a very large extent, to the excellent adhesive properties of organic polyisocyanates. At the same time, however, these adhesive properties can be a disadvantage in that they cause severe sticking of the ligno-cellulosic material to the hot metal surfaces with which it comes into contact during the hot-pressing operation. The product can be harmed in this way or even rendered entirely worthless and the subsequent cleaning of the contaminated surfaces is difficult, time-consuming and costly.

In order to minimise this adhesion problem it has been proposed in our United Kingdom Patent Application No. 8026057 published as No. 2081637A to hot press the ligno-cellulosic material in contact with the organic polyisocyanate and also a vegetable wax or a modified vegetable oil, said wax or modified oil having a melting point of at least 70° C. In that process, the wax or modified oil, being intimately mixed with the ligno-cellulosic material and the polyisocyanate, acts as an internal release agent and is extremely effective in minimising unwanted adhesion to caul plates, press parts and other surfaces with which the treated ligno-cellulosic material may come into contact.

Other types of wax are proposed as internal release agents in our United Kingdom Patent Applications Nos. 8027449 and 8040958.

In the aforementioned patent applications, it is proposed to apply the wax to the ligno-cellulosic material in the form of a solution in an organic solvent which may be the polyisocyanate or in the form of an aqueous dispersion which may also contain the polyisocyanate.

Since the essential adhesive agent is the polyisocyanate, there is some advantage in having the release agent incorporated therein. In some cases, however, it is difficult to form a satisfactory solution or dispersion of the wax in the polyisocyanate.

It has now been found that waxes may be satisfactorily dispersed in liquid organic polyisocyanates in the presence of certain liquid esters. The term "liquid" in this connection indicates the physical state of the polyisocyanate and the ester at normal ambient temperatures.

Thus according to the invention, there is provided an organic polyisocyanate composition containing, on a weight basis, from 99 to 60 parts of a liquid organic polyisocyanate and from 1 to 40 parts of a mixture of a wax and a liquid ester having a molecular weight of at least 250, wherein the wax and the liquid ester are present in the proportions of from 90:10 to 10:90.

Particularly suitable compositions are those containing, on a weight basis, from 90 to 75 parts of the liquid organic polyisocyanate and from 10 to 25 parts of the mixture of wax and liquid ester. Particularly suitable mixtures of wax and liquid ester contain from 37.5 to 75 parts of wax and from 62.5 to 25 parts of ester.

Suitable liquid polyisocyanates for use in the compositions of the invention include diisocyanates and high functionality isocyanates, particularly aromatic polyisocyanates. Mixtures of polyisocyanates may be used of which the crude mixtures of di- and higher functionality polyisocyanates produced by phosgenation of aniline/formaldehyde condensates, known as crude MDI, are especially suitable. The organic polyisocyanates may be isocyanate-ended prepolymers made by reacting an excess of a diisocyanate or higher functionality polyisocyanate with a polyol. The organic polyisocyanate may advantageously be in a water-emulsifiable form as has been described in our UK Patent Specification No. 1444933 and UK Patent Application 2018796A.

Waxes which may be used in the compositions of the invention include vegetable waxes having melting points of at least 70° C., for example carnauba wax, modified vegetable oils having melting points of at least 70° C., for example hydrogenated castor oil, microcrystalline waxes having melting points of at least 70° C., for example Bareco and Amsco waxes, mineral waxes having melting points of at least 70° C., for example Montan wax (a mineral was obtained from lignite) and animal waxes having melting points of at least 60° C., for example beeswax or Shellac. Synthetic or modified animal waxes having a melting point of at least 60° C. such as pentaerythritol tetra stearate or commercially available synthetic waxes may also be used. Mixtures of waxes may be used if desired, for example the wax available as Faradaywax which is a mixture of beeswax and carnauba wax.

Liquid esters having molecular weights above 250 which may be used in the compositions of the invention include alkyl, benzyl and polyoxyalkylene esters of long-chain aliphatic carboxylic acids such as lauric and oleic acids. Examples of especially suitable esters include octan-1-ol oleate (n-octyl oleate).

Especially preferred are alkyl esters of aliphatic carboxylic acids derived from an alkyl alcohol containing from 3 to 30 carbon atoms and a saturated or unsaturated fatty acid containing from 10 to 25 carbon atoms for example lauric or oleic acid. Examples of suitable alkyl alcohols include n-octyl, lauryl, n-hexyl and 2-ethylhexyl alcohols.

The liquid ester may be a fully esterified product or a partially esterified product. For example the ester may have an acid value of from 0 to 30 mg potassium hydroxide per g and a hydroxyl value of from 0 to 20 mg potassium hydroxide per g. An acid value of from 10 to 30 mg potassium hydroxide per g and a hydroxyl value of from 2 to 20 mg potassium hydroxide per g is preferred as these esters have been found to achieve an especially effective wax dispersion without imparing the emulsion characteristics of the isocyanate, and consequently give especially good release properties with good physical properties of the manufactured moulded body. When n-octyl oleate is used as the ester the acid value is preferably from 10 to 20 mg potassium hydroxide per g and the hydroxyl value is preferably for 2 to 8 mg potassium hydroxide per g.

The compositions of the invention may be prepared by mixing the components together at such a temperature that the wax is in a liquid state. Thus, the polyisocyanate, wax and ester may be stirred together at a temperature in the range 70°–180° C., preferably 90°–120° C., the dispersion then being cooled below 50° C. Alternatively, the wax and ester may be stirred together at a temperature in the range 90°–120° C. to give a blend which is then stirred into the diisocyanate at the same temperature, the dispersion then being cooled below 50° C. If desired, a colouring matter may be added to the compositions of the invention to distinguish them from unmodified polyisocyanates.

The organic polyisocyanate compositions of the invention are suitable for use in a process for the manufacture of sheets or moulded bodies which comprises hot-pressing a ligno-cellulosic material in contact with the said polyisocyanate composition.

Whilst the said process is particularly suitable for the manufacture of the particle board known extensively as chipboard and will be largely described with reference to such manufacture, it is not to be regarded as limited in that respect and can also be used in the manufacture of medium density fibre board, wafer board, mouldings by the Werzalit process and plywood. Thus, the ligno-cellulosic material used can include wood chips, wood fibres, shavings, veneers, wood wool, cork, bark, sawdust and like waste products of the woodworking industry as well as other materials having a ligno-cellulosic basis such as bagasse, straw, flax, sisal, hemp, rushes, reeds and grasses. Additionally, there may be mixed with the lignocellulosic material, other particulate or fibrous materials such as glass fibre, mica, asbestos, rubber and plastics materials.

The process is readily carried out by applying the organic polyisocyanate composition of the invention to the ligno-cellulosic material and then subjecting the treated material to heat and pressure. The polyisocyanate compositions may be applied in such an amount to give a weight ratio of polyisocyanate to ligno-cellulosic material in the range 0.1:99.9 to 20:80, preferably 0.5:99.5 to 7.0:93.

If desired, other conventional binding agents, such as formaldehyde condensate adhesive resins, may be used in conjunction with the polyisocyanate composition.

In particleboard manufacture, the ligno-cellulosic material and polyisocyanate may be conveniently mixed by spraying the polyisocyanate composition on to the ligno-cellulosic material while it is being agitated in an enclosed mixer either of a single batch type or a continuous type. The polyisocyanate composition may be employed as such or in the form of a solution in an organic solvent but preferably it is employed in the form of an aqueous emulsion. Suitable emulsions may be prepared by stirring the polyisocyanate composition with water in the presence of an emulsifying agent. If an emulsifiable polyisocyanate of the type described above is present in the polyisocyanate composition, no further emulsifying agent need be added when preparing the aqueous emulsion. If the polyisocyanate present in the polyisocyanate composition is not of an emulsifiable type, an external emulsifying agent needs to be used.

The ligno-cellulosic material after treatment with the polyisocyanate composition of the invention may be sprinkled on to caul plates, usually made of aluminium or steel, which serve to carry the "furnish" into the press where it is compressed to the desired extent, usually at a temperature between 140° and 230° C. In the absence of an efficient release agent the ligno-cellulosic material adheres strongly to the caul plates and/or the platens of the press. When using the polyisocyanate compositions of the present invention, the adhesion of particles of the ligno-cellulosic material to the metal surfaces is reduced to a negligible extent. This is so even when the surfaces are already contaminated with resinous materials or their degradation products. At the start of a manufacturing run it is helpful, but not essential, to condition the caul plates using a wax or modified oil of the type used in the compositions of the invention. The conditioned plates may then be used a large number of times in the process of the invention without further treatment.

We have found that a continuously operated particleboard press using conventional urea formaldehyde binder may be converted to operation using the dispersions of the present invention by progressively replacing the urea formaldehyde feed by the feed of the present invention.

Other methods of manufacturing particleboard include depositing the treated ligno-cellulosic material on to conveyor belts for transfer to the press and here again the compositions of the invention are advantageous in minimising adhesion of the ligno-cellulosic material to the belts and press.

More detailed descriptions of methods of manufacturing particleboard and similar products based on ligno-cellulosic material are available in the prior art. The techniques and equipment conventionally used can be adapted for use with the compositions of the invention.

In some manufacturing situations, the treated ligno-cellulosic material may come into contact with materials other than those specifically mentioned above, for example brass, chrome plated surfaces and plastics materials. In such situations, the compositions of the invention are again remarkably effective in minimising unwanted adhesion.

The sheets and moulded bodies produced from the compositions of the invention have excellent mechanical properties and they may be used in any of the situations where such articles are customarily used.

The invention is illustrated but not limited by the following Examples in which all parts and percentages are by weight.

EXAMPLE 1

An emulsifiable isocyanate is prepared by reacting 3 parts of methoxy polyethylene glycol (molecular weight 650) with 97 parts of crude MDI having an NCO content of 30% and containing approximately 50% of diphenylmethane diisocyanates, the remainder being polymethylene polyphenyl polyisocyanates of higher functionality.

To 80 parts of the emulsifiable isocyanate at 90° C., a blend of 7.5 parts Montan wax and 12.5 parts of octan-1-ol oleate is charged and stirred at 90°–95° C. for approximately 1 hour then cooled with stirring to below 50° C. The product is a liquid which when used as the binder (aqueous emulsion) in the preparation of particle board gives release from previously conditioned caul plates.

The number of releases obtained without further conditioning of the caul plates is in excess of 20, this number being limited only by the time scale for the trial.

EXAMPLE 2

To 80 parts of the emulsifiable isocyanate described in Example 1, 10 parts of octan-1-ol oleate and 10 parts of Montan wax are charged at 90° C. and the mixture heated to 120° C. with stirring and maintained on temperature for 1 hour. The mixture is then cooled with stirring to below 50° C. to yield a mobile liquid containing finely divided particles of wax. This diisocyanate when emulsified with water yields an emulsion with a pot-life in excess of 2 hours. On use of the diisocyanate as the binder (aqueous emulsion) in the preparation of particle board, excellent release is achieved from previously conditioned caul plates.

The number of releases is limited only by the time scale for the trial.

EXAMPLE 3

To 77.6 parts of crude MDI, having an isocyanate content of 30%, was added 2.4 parts of monomethoxylated polyethylene glycol (MOPEG) of molecular weight 650 and 10 parts of n-octyl oleate having an acid value of 15.0 mg KOH/g and a hydroxyl value of 4.9 mg KOH/g. The crude MDI contained approximately 50% of diphenylmethane diisocyanate, the remainder being polymethylene polyphenyl polyisocyanates of higher functionality. The mixture was heated to 90° to 95° C. and 10 parts of Montan wax was slowly added with agitation. The temperature was raised to 120° C. and the mixture was maintained at this temperature for 2 hours before cooling to below 35° C. with continuous agitation.

The emulsifiable isocyanate containing the wax release agent prepared as above was emulsified in water in the proportion 3.125 parts isocyanate to 10 parts water. This aqueous emulsion was applied to 102 parts of 50/50 10:25 mesh pine/spruce wood chips having a moisture content of 2%, and the resultant mixture was used as a surface material in the manufacture of particleboards.

For the core material, 3.125 parts of the emulsifiable isocyanate was emulsified in 10 parts water, and applied to 102 parts of pine/spruce wood which in this case had a particle size of 5 mesh.

A series of boards were prepared from ⅔ core material and ⅓ surface material. Thus half of the surface material was sprinkled into a former placed on an aluminium plate. This was followed by the core material and the remainder of the surface material. The resultant "furnish" was then hand pressed to form a "cake" which was introduced into the press. Steel spacers were placed on the aluminium plate and a steel plate placed on top of the cake. Pressure was applied at a press temperature of 175° C. until both plates were in contact with the spacers. Pressure of 450 to 550 psi was maintained for a pressing time of 15 secs/mm board thickness. 20 Boards were manufactured in this manner, and effective release of the boards from the press was achieved throughout the run and was still being achieved when the run was terminated.

Typical physical properties of the boards produced are given in Table 1.

EXAMPLE 4

The procedure of Example 3 was repeated except that the ratio of the emulsifiable isocyanate containing the wax release agent to the water was 7.5 parts to 10 parts water.

As before, good release was obtained throughout a 20 board run, and typical properties are presented in Table 1.

EXAMPLE 5

The procedure of Example 3 was repeated except that flaked beech wood having a moisture content of 2% was used in place of the pine/spruce wood. The ratio of the emulsifiable isocyanate containing the wax release agent to the water was 3.125 parts isocyanate to 12 parts water. This emulsion was added to 102 parts wood, and the resultant material used for both core and surface of the board.

Good release was obtained throughout a 20 board run, and typical properties of the resultant boards are presented in Table 1.

EXAMPLE 6

The procedure of Example 5 was repeated except that the ratio of the emulsifiable isocyanate containing the wax release agent to the water was 7.5 parts to 12 parts water.

As before, good release was obtained throughout a 20 board run.

TABLE 1

| Example | Density (kg/m$^3$) | "V20" Tensile Strength (kN/m$^2$) | "V100" Tensile Strength (kN/m$^2$) |
|---|---|---|---|
| 3 | 720 | 970 | — |
| 4 | 720 | 1500 | 500 |
| 5 | 690 | 530 | — |

EXAMPLES 7 to 22

The general procedure of Example 3 was repeated for a variety of different waxes and different liquid esters.

Thus an emulsifiable isocyanate containing 10 parts of the wax and 10 parts of the liquid ester was prepared as in Example 3 and was applied to 102 parts 50/50 10/25 mesh pine/spruce wood having a moisture content of 2%. Two alternative proportions were used:

(A) 3.125 parts isocyanate emulsified in 10 parts water and added to 102 parts wood; or (B) 7.5 parts isocyanate emulsified in 10 parts water and added to 102 parts wood.

This material was used for the surface of the boards.

For the core material, an emulsifiable isocyanate was used which contained neither wax nor liquid ester. Thus 3 parts of the MOPEG was added to 97 parts of the crude MDI, and the mixture was heated to 60° C. with agitation. The mixture was maintained at this temperature for 2 hours and then cooled under continuous agitation. The resultant emulsifiable isocyanate was added to 5 mesh pine/spruce wood having a moisture content of 2% to form the core material. When the proportions used in the surface material were those given as (A) above, the proportions used in the core material were:

(A') 2.5 parts isocyanate emulsified in 10 parts water and applied to 102 parts wood.

When the proportions used in the surface material were those given as (B) above, the proportions used in the core material were:

(B') 6 parts of isocyanate emulsified in 10 parts of water and applied to 102 parts wood.

Boards were prepared from the surface and core material as described in Example 3. 20 Boards were manufactured in this manner and effective release of the boards from the press was achieved throughout the run and was still being achieved when the run was terminated.

The materials used and the resultant physical properties of the boards produced are given in Table 2.

TABLE 2

| Example | Wax | Liquid Ester | Acid Value mg KOH/g | Hydroxyl Value mg KOH/g | Proportions Surface/Core | Density Kg/m$^3$ | "V20" Tensile Strength kN/m$^2$ | "V100" Tensile Strength kN/m$^2$ |
|---|---|---|---|---|---|---|---|---|
| 7 | Montan | n-octyl oleate | 15.0 | 4.9 | A/A' | 700 | 920 | |
| 8 | " | n-octyl oleate | 15.0 | 4.9 | B/B' | 680 | 1400 | 430 |
| 9 | " | lauryl oleate | 20.2 | 16.3 | A/A' | 720 | 1000 | |
| 10 | " | lauryl oleate | 20.2 | 16.3 | B/B' | 730 | 1600 | 460 |
| 11 | " | n-hexyl oleate | 24.9 | 7.2 | A/A' | 720 | 990 | |
| 12 | " | n-hexyl oleate | 24.9 | 7.2 | B/B' | 720 | 1700 | 240 |
| 13 | Carnauba | n-octyl oleate | 15.0 | 4.9 | A/A' | 730 | 1000 | |
| 14 | " | n-octyl oleate | 15.0 | 4.9 | B/B' | 690 | 1500 | 155 |
| 15 | Faraday | n-octyl oleate | 15.0 | 4.9 | A/A' | 720 | 810 | |
| 16 | " | n-octyl oleate | 15.0 | 4.9 | B/B' | 700 | 1300 | 145 |
| 17 | Montan | 2-ethyl hexyl oleate | | | A/A' | 690 | 240 | |
| 18 | " | 2-ethyl hexyl oleate | | | B/B' | 700 | 1350 | 380 |
| 19 | Penta-erythritol tetra-stearate | n-octyl oleate | 15.0 | 4.9 | A/A' | 700 | 730 | |
| 20 | Penta-erythritol tetra-stearate | n-octyl oleate | 15.0 | 4.9 | B/B' | 700 | 1050 | 290 |
| 21 | Hoechst wax KSE | n-octyl oleate | 15.0 | 4.9 | A/A' | 680 | 340 | |
| 22 | Hoechst wax KSE | n-octyl oleate | 15.0 | 4.9 | B/B' | 700 | 1300 | 220 |

EXAMPLES 23 AND 24

The procedure of Example 7 was repeated except that 2 parts of commercial 50% solids aqueous wax emulsion was added to the aqueous emulsion of the isocyanate before it was added to the core material.

The procedure was repeated (Example 24) using the proportions of B/B' of Example 8.

Effective release was achieved for a full run of 20 boards, and the typical physical properties of the boards are given in Table 3.

EXAMPLES 25 AND 26

The procedure of Example 7 was repeated except that 1 part of commercial 50% solids aqueous wax emulsion was added to the aqueous emulsion of the isocyanate before it was added to the surface material.

The procedure was repeated (Example 26) using the proportions B/B' of Example 8.

Effective release was achieved for a full run of 20 boards, and typical physical properties of the boards are given in Table 3.

EXAMPLE 27

The procedure of Example 7 was repeated except that emulsifiable isocyanate used in the surface material was prepared using 87.3 parts of crude MDI, and 2.7 parts of MOPEG with 5 parts of n-octyl oleate and 5 parts of shellac wax. The surface material was prepared from 2.78 parts of the above isocyanate emulsified in 10 parts of water and applied to 102 parts of 50/50 10:25 mesh pine/spruce wood.

The core material was prepared as in Example 7 except that 2.5 parts of emulsifiable isocyanate was emulsified in 10 parts of water and applied to 102 parts 5 mesh pine/spruce wood.

Effective release was achieved for a full run of 20 boards, and typical physical properties of the boards produced are given in Table 3.

EXAMPLE 28

The procedure of Example 27 was repeated except that the proportions employed were:

Surface material: 6.67 parts isocyanate emulsified in 10 parts water and applied to 102 parts wood.

Core material: 6 parts isocyanate emulsified in 10 parts water and applied to 102 parts wood.

Effective release was achieved for a full run of 20 boards, and typical physical properties of the boards produced are given in Table 3.

EXAMPLES 29 AND 30

The procedure of Example 7 was repeated except that the isocyanate used in the surface material was a polymeric MDI of viscosity approximately 4 poise, commercially available as SUPRASEC VM 100.

The procedure was repeated (Example 30) using the proportions B/B' of Example 8.

Effective release was obtained for a full run of 20 boards, and typical physical properties of the boards produced are given in Table 3.

EXAMPLES 31 AND 32

The procedure of Example 7 was repeated except that the isocyanate used in the surface material was a high viscosity polyfunctional diphenylmethane diisocyanate of viscosity approximately 15 poises at 25° C.

The procedure was repeated (Example 32) using the proportions B/B' of Example 8.

Effective release was obtained for a full run of 20 boards.

TABLE 3

| Example | Density Kg/m$^3$ | "V20" Tensile Strength kN/m$^2$ | "V100" Tensile Strength kN/m$^2$ |
|---|---|---|---|
| 23 | 690 | 890 | — |
| 24 | 700 | 1450 | 280 |
| 25 | 700 | 1000 | — |
| 26 | 700 | 1550 | 450 |
| 27 | 710 | 890 | — |
| 28 | 710 | 1600 | 135 |
| 29 | 670 | 700 | — |
| 30 | 720 | 1250 | 400 |

EXAMPLE 33

The procedure of Example 8 was repeated except that both the surface and core materials were stored after application of the isocyanate and before pressing.

The physical properties of the boards produced are given below for the different storage times after application of the isocyanate and before pressing.

| Storage time (hours) | 20 | 2 | 4 |
|---|---|---|---|
| Density (Kg/m$^3$) | 762 | 684 | 675 |
| "V20" Tensile strength (kN/m$^2$) | 1740 | 1389 | 1178 |
| "V100" Tensile strength (kN/m$^2$) | 435 | 384 | 296 |

In each case no difficulties were encountered in the release of the boards from the press.

EXAMPLE 34

Production on a traybelt Siempelkamp system was converted from operation using conventional urea formaldehyde resins to operation using the process of the present invention. The production line was "conditioned" in the following manner. Three layer boards 16 mm thickness were manufactured from wood furnish (larch/spruce/miscellaneous timber 60:30:10) with the surface layer and core layer containing 12% and 8% respectively conventional solid urea formaldehyde resin plus catalyst. The core layer binder glue was then converted to 2.8% of the emulsifiable isocyanate used for the core layer in Example 7 moisture content 9–10% (all based on dry wood weight) by preparing the glue emulsion on line and applying it to the wood via the core Drais blender. The surface layer wood binder glue was also adjusted to give 8% of a urea formaldehyde resin solids (plus catalyst), 1.08% of the emulsifiable isocyanate used for the surface layer in Example 7 and a total moisture content of the wood after spraying the emulsion of 11–12% (all based on dry wood content). The glue emulsion being prepared in line and applied to the wood chip via the surface Drais blender.

Using this composition, ten boards were prepared on each contact surface in the multi-daylight press; the press temperature being 175°–180° C. After completion of the ten releases per contact surface the surface glue emulsion composition was modified to 6% solids urea formaldehyde resin (plus catalyst), 1.62% surface isocyanate emulsion and moisture content 11–12%. A further 10 boards per contact surface were prepared and after completion the surface glue was further modified to urea formaldehyde resin 4% solids resin (plus catalyst), 2.16% surface isocyanate emulsion moisture content 11–12%. After the preparation of a further 10 boards per contact surface in the press, the press was considered to be "conditioned". All isocyanate bonded board was then prepared, no adhesion occurring on continuous production over a period of six days. The production only being terminated by the length of time agreed for the trial.

Typical board properties for 16 and 18 mm board and differeing binder levels are as follows:

(A)
Surface layer 3.2% emulsifiable isocyanate of the surface layer of Example 7.
Core layer 2.8% emulsified isocyanate of the core layer of Example 7.
16 mm board density 662 Kg/m$^3$ dry internal bond (V20) 5.36 kN/m$^2$ (B)
Surface layer 7.0% emulsifiable isocyanate
Core layer 5.0% emulsifiable isocyanate
18 mm board density 746 Kg/m$^3$ dry internal bond (V20) 1516 kN/m$^3$ wet internal bond (V100) 266 kN/m$^3$

EXAMPLES 35 AND 36

Straw was dried to 2% moisture content and glue applied in a rotary gluer (i.e. rotating drum with one static hydraulic spray) using the following compositions:

EXAMPLE 35

Straw 2% moisture—13.26 kg
Emulsifiable isocynate used for the surface layer in Example 7—0.845 kg
Water—0.91 liters
Isocyanate composition content on straw—6.5%
Total moisture content—9%

EXAMPLE 36

Straw 3% moisture—13.38 kg
Emulsifiable isocyanate used for the surface layer in Example 7—0.286 kg
Water—0.286 kg
Urea formaldehyde (Solid)—0.91 kg
Isocyanate composition content on straw—2.2%
Urea formaldehyde content on straw—7%
Total moisture content—11%

EXAMPLE 35

The glued straw was hammer milled and then the furnish formed by hand. The furnish was pressed to form 12 mm board using a pressing schedule of 16 secs/mm at 175° C. producing a board of 630 kg/m$^3$ density. The board properties were of good apparent strength with no springback and good release.

EXAMPLE 36

A batch of glued straw was prepared using the urea formaldehyde/isocyanate composition, the preparation was as with Example 35 other than that the straw was hammer milled before and after gluing.

The pressing conditions were as previous and again good board was produced and good release achieved.

EXAMPLE 37

The conventional fibre feedstock for medium density fibreboard (1% moisture) was sprayed with the isocyanate emulsion used for the surface layer in Example 7 in a rotary blender (i.e. rotating drum with one static hydraulic spray). The furnish was formed on an MDF former and built up to produce boards of 5 mm, 12 mm and 19 mm final thickness.

Actual conditions were:
Fibre (1% moisture)—12.12 kg
Emulsifiable isocyanate composition—0.6 kg
Water—0.84 liters
% Emulsifiable isocyanate composition on dry fibre—5%
% total moisture on dry fibre—8%
Press time—16 secs/mm
Press temperature—175° C.

Good quality boards showing good release were achieved.

EXAMPLES 38 TO 40

The general procedure of Example 3 was used to manufacture particleboards from isocyanate emulsions according to the present invention, prepared in a variety of different ways. In each case the isocyanate emulsion was prepared from the emulsifiable isocyanate used for the core material in Example 7, n-octyl oleate having an acid value of 15.0 mg KOH/g and a hydroxyl value of 4.9 mg KOH/g and Montan wax. The isocyanate emulsion was used to manufacture single layer particleboard having 5 mesh pine/spruce chips throughout.

In each case a trial run of 20 boards operated satisfactorily and good release was achieved from steel and aluminium plates throughout the run and was still being achieved at the termination of the run.

EXAMPLE 38

80 parts of emulsifiable isocyanate was charged into a vessel fitted with an agitator. The temperature was raised to 95° C. A mixture of 10 parts Montan wax with 10 parts n-octyl oleate, also at 95° C., was charged into the vessel. Agitation was continued whilst allowing the mix to cool to room temperature.

EXAMPLE 39

80 parts of emulsifiable isocyanate was charged into a vessel fitted with an agitator. The temperature was raised to 95° C. A mixture of 10 parts Montan wax with 10 parts n-octyl oleate, also at 95° C. was charged into the vessel. The temperature was raised to 120° C. and held at that temperature for 2 hours. The product was then allowed to cool with continuous agitation.

EXAMPLE 40

80 parts of emulsifiable isocyanate was charged into a vessel together with 10 parts n-octyl oleate. The temperature was raised to 95° C. and 10 parts of solid Montan wax at room temperature were introduced with agitation taking care to keep the temperature in a range of 90°-95° C. The temperature was then raised to 120° C. and kept at this temperature for 2 hours. The product was then allowed to cool with continuous agitation.

EXAMPLE 41

77.6 parts crude MDI having an isocyanate content of 30% together with 1.2 parts MOPEG of molecular weight 550, 1.2 parts MOPEG of molecular weight 750 and 10 parts n-octyl oleate were charged into a vessel fitted with an agitator. The temperature was raised to 950° C. with agitation. 10 parts of solid Montan wax at room temperature were introduced taking care to keep the temperature in a range of 90°-95° C. The temperature was then raised to 120° C. and kept at this temperature for 2 hours. The product was then allowed to cool with continuous agitation. The resultant emulsion was used to manufacture 20 particleboards as in Examples 38 to 40 and excellent release was obtained.

EXAMPLE 42

80 parts crude MDI having an isocyanate content of 30% together with 10 parts n-octyl oleate were heated to 90°-95° C. with agitation. 10 parts Montan wax were added and the temperature raised to 120° C. and kept at this temperature for 2 hours. The product was allowed to cool with continuous agitation. 1.2 parts MOPEG of molecular weight 550 and 1.2 parts MOPEG of molecular weight 750 were added. The product was heated to 120° C. and then cooled with continuous agitation. The resultant emulsion was used to manufacture 20 particleboards as in Examples 38 to 40 and excellent release was obtained.

We claim:

1. A disperable organic polyisocyanate composition comprising, on a weight basis, from 99 to 60 parts of an emulsifiable liquid organic polyisocyanate and from 1 to 40 parts of a mixture of (a) a wax selected from the group consisting of a vegetable wax having a melting point of at least 70° C., a modified vegetable oil having a melting point of at least 70° C., a microcrystalline wax having a melting point of at least 70° C., an animal wax having a melting point of at least 60° C., a synthetic wax having a melting point of at least 60° C., a modified animal wax having a melting point of at least 60° C. and mixtures thereof and (b) a liquid ester having a molecular weight of at least 250 derived from a monohydric alkyl alcohol containing from 3 to 30 carbon atoms and a saturated or unsaturated monocarboxylic fatty acid containing from 10 to 25 carbon atoms, wherein the wax and the liquid ester are present in the proportions of from 90:10 to 10:90, the composition having mold release properties when used in the form of an aqueous dispersion as binder in the manufacture of sheets or molded bodies by the hot pressing of lignocellulosic material.

2. A composition according to claim 1 wherein the mixture of the wax and liquid ester contains from 37.5 to 75 parts of the wax and from 62.5 to 25 parts of the ester.

3. A composition according to claim 1 wherein the ester has an acid value of from 0 to 30 mg potassium hydroxide per gram and a hydroxyl value of from 0 to 20 mg potassium hydroxide per gram.

4. A composition according to claim 3 wherein the ester has an acid value of from 10 to 30 mg potassium hydroxide per gram and a hydroxyl value of from 2 to 20 mg potassium hydroxide per gram.

5. A composition according to claim 1 wherein the ester is n-octyl oleate.

6. A composition according to claim 5 wherein the ester has an acid value of from 10 to 20 mg potassium hydroxide per gram and a hydroxyl value of from 2 to 8 mg potassium hydroxide per gram.

* * * * *